(12) United States Patent
Lovhaug (10) Patent No.: US 7,763,234 B2
(45) Date of Patent: Jul. 27, 2010

(54) PHARMACEUTICAL COMPOUNDS

(75) Inventor: Dagfinn Lovhaug, Oslo (NO)

(73) Assignee: GE Healthcare AS, Oslo (NO)

( * ) Notice: Subject to any disclaimer, the term of this patent is extended or adjusted under 35 U.S.C. 154(b) by 995 days.

(21) Appl. No.: 10/591,047

(22) PCT Filed: Mar. 3, 2005

(86) PCT No.: PCT/NO2005/000078

§ 371 (c)(1), (2), (4) Date: Aug. 29, 2006

(87) PCT Pub. No.: WO2005/084715

PCT Pub. Date: Sep. 15, 2005

(65) Prior Publication Data

US 2007/0297979 A1  Dec. 27, 2007

(30) Foreign Application Priority Data

Mar. 4, 2005  (NO)  ................................. 20040953

(51) Int. Cl.
*A61K 51/00* (2006.01)
*A61M 36/14* (2006.01)

(52) U.S. Cl. .................... 424/1.69; 424/1.11; 424/1.65; 424/1.81; 424/9.4

(58) Field of Classification Search ................ 424/1.11, 424/1.49, 1.65, 1.69, 1.81, 1.85, 1.89, 9.1, 424/9.3, 9.4, 9.5, 9.6, 9.7, 9.8; 534/7, 10–16; 530/300, 317, 324–331, 333, 338

See application file for complete search history.

(56) References Cited

U.S. PATENT DOCUMENTS 3,966,896 A  6/1976  Glovsky

FOREIGN PATENT DOCUMENTS

| | | |
|---|---|---|
| WO | 93/12819 | 7/1993 |
| WO | 98/18496 | 5/1998 |
| WO | 02/20610 | 3/2002 |
| WO | 03/006491 | 1/2003 |
| WO | 2004/062568 | 7/2004 |

OTHER PUBLICATIONS

Chauveau, D. et.al. "Investigation of the biochemical effects of rennin inhibition in normal volunteers treated by an ACE inhibitor" BR. J. Clin. Pharmac, vol. 33, 1992, pp. 253-260.

Glossmann, H. et.al., "Properties of angiotensin II receptors in the bovine and rat adrenal cortex" Journal of Biological Chemistry, vol. 249, 1974, pp. 825-834.

Liu, S. et. al. "TC-labellled small peptides as diagnostic radiopharmaceuticals" Chemical Reviews, ACS, Washington, D.C., vol. 99, No. 9, Sep. 1999 pp. 2235-2268.

Baker, K.M. et.al. "Cardiac and vascular actionso fdecapeptide agiotensin analogs" Journal of Pharmacology and Experimental Therapeutics, vo. 239, No. 3, 1986 pp. 790-796.

Borgheresi, R.A.M.B., et.al. "Isolation and identification of angiotensin-like peptides from the plasma of the snake bothrops jararaca" Comp Biochem Physiol, vol. 113B. No. 3, 1996 pp. 467-473.

PCT/NO2005/000078 ISR dated Nov. 2005.
PCT/NO2005/000078 IPER dated May 2006.

*Primary Examiner*—D L Jones
(74) *Attorney, Agent, or Firm*—Craig Bohlken (57) ABSTRACT

A pharmaceutical of the general formula $Z—(L)_n-V$, wherein V denotes an amino acid sequence $X^1-X^2$-Val-Tyr-Ile-His-Pro-$X^8$-$X^9$-$X^{10}$; L denotes a bond or a linker; Z denotes a group that optionally can carry an imaging moiety M; $X^1$ denotes an amino acid; $X^2$ denotes Arg or N-alkylated Arg or a mimetic of Arg; $X^8$, $X^9$ and $X^{10}$ constitute an ACE cleavage site; Z forms a bond with the amino acid $X^1$ optionally through the linker L; and M where denotes an imageable moiety capable of detection either directly or indirectly in a diagnostic imaging procedure.

8 Claims, 1 Drawing Sheet

FIG. 1

SEQUENCE LISTING

```
<160> NUMBER OF SEQ ID NOS: 8

<210> SEQ ID NO 1
<211> LENGTH: 10
<212> TYPE: PRT
<213> ORGANISM: Artificial sequence
<220> FEATURE:
<223> OTHER INFORMATION: Synthesised peptide
<220> FEATURE:
<221> NAME/KEY: Misc_feature
<222> LOCATION: (1)..(1)
<223> OTHER INFORMATION: Any amino acid
<220> FEATURE:
<221> NAME/KEY: Misc_feature
<222> LOCATION: (2)..(2)
<223> OTHER INFORMATION: Arg, N-alcylated Arg or a mimetic thereof
<220> FEATURE:
<221> NAME/KEY: Misc_feature
<222> LOCATION: (8)..(8)
<223> OTHER INFORMATION: Gly, Phe or an amino acid containing an
      aromatic or aliphatic side-chain
<220> FEATURE:
<221> NAME/KEY: Misc_feature
<222> LOCATION: (9)..(9)
```

```
<223> OTHER INFORMATION: Pro, Arg, His, Ala, Phe, Glu, Leu, Val, Ile,
      Met, Trp, Asp or Lys
<220> FEATURE:
<221> NAME/KEY: Misc_feature
<222> LOCATION: (10)..(10)
<223> OTHER INFORMATION: Pro, Arg, His, Ala, Phe, Glu, Leu, Val, Ile,
      Met, Trp, Asp or Lys

<400> SEQUENCE: 1

Xaa Xaa Val Tyr Ile His Pro Xaa Xaa Xaa
1               5                   10

<210> SEQ ID NO 2
<211> LENGTH: 10
<212> TYPE: PRT
<213> ORGANISM: Angiotensin I sequence

<400> SEQUENCE: 2

Gly Arg Val Tyr Ile His Pro Phe His Leu
1               5                   10

<210> SEQ ID NO 3
<211> LENGTH: 10
<212> TYPE: PRT
<213> ORGANISM: Arificial sequence

<400> SEQUENCE: 3

Gly Arg Val Tyr Ile His Pro Ile His Leu
1               5                   10

<210> SEQ ID NO 4
<211> LENGTH: 9
<212> TYPE: PRT
<213> ORGANISM: Arificial sequence
<220> FEATURE:
<221> NAME/KEY: MISC_FEATURE
<222> LOCATION: (7)..(7)
<223> OTHER INFORMATION: Amino acid in position 7 is Bip
      2-amino-3-biphenyl propionoc acid

<400> SEQUENCE: 4

Arg Val Tyr Ile His Pro Xaa His Leu
1               5

<210> SEQ ID NO 5
<211> LENGTH: 10
<212> TYPE: PRT
<213> ORGANISM: Artificial sequence
<220> FEATURE:
<223> OTHER INFORMATION: Synthesised peptide
<220> FEATURE:
<221> NAME/KEY: MISC_FEATURE
<222> LOCATION: (8)..(8)
<223> OTHER INFORMATION: Amino acid in position 8 is Bip
      2-amino-3-biphenyl propionic acid

<400> SEQUENCE: 5

Gly Arg Val Tyr Ile His Pro Xaa His Leu
1               5                   10
```

```
<210> SEQ ID NO 6
<211> LENGTH: 10
<212> TYPE: PRT
<213> ORGANISM: Artificial sequence
<220> FEATURE:
<223> OTHER INFORMATION: Synthesised peptide
<220> FEATURE:
<221> NAME/KEY: MISC_FEATURE
<222> LOCATION: (8)..(8)
<223> OTHER INFORMATION: Amino acid in position 8 is Hph
      2-amino-4-phenyl butanoic acid

<400> SEQUENCE: 6

Gly Arg Val Tyr Ile His Pro Xaa His Leu
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthesised peptide
<220> FEATURE:
<221> NAME/KEY: MISC_FEATURE
<222> LOCATION: (8)..(8)
<223> OTHER INFORMATION: Amino acid in position 8 is Phg
      2-amino-2-phenyl acetic acid

<400> SEQUENCE: 7

Gly Arg Val Tyr Ile His Pro Xaa His Leu
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Angiotensin II sequence

<400> SEQUENCE: 8

Asp Arg Val Tyr Ile His Pro Phe
1               5
```

PHARMACEUTICAL COMPOUNDS

FIELD OF INVENTION

The present invention relates to novel pharmaceuticals suitable for use in the treatment of heart failure, cardiac arrhythmia and other diseases where fibrosis is prominent and in the diagnosis of heart failure and other diseases where fibrosis is prominent. More specifically the invention relates to pharmaceuticals useful in treatment and diagnosis of diseases associated with the up-regulation of the Angiotensin II receptor, $AT_1$ and Angiotensin Converting Enzyme, ACE. The pharmaceuticals of the present invention are converted into its active form (i.e. the $AT_1$ targeting form) by cleavage by ACE in vivo.

Diseases, which can be detected by the use of imaging agents targeting the AT1 receptor, are congestive heart failure (CHF), arteriosclerosis and other diseases and conditions where a fibrotic process is prominent.

The pharmaceuticals comprise a peptidic Angiotensin I (Ang I) analogue with an ACE cleavage site, further the pharmaceuticals comprises a group which can carry a diagnostically imageable moiety and an optional linker. After cleavage with ACE active pharmaceuticals comprising an Angiotensin II (Ang II) analogue, a group capable of carrying a diagnostically imageable moiety and an optional linker is formed. The imaging agent has affinity for the Angiotensin receptors, in particularly for the Angiotensin II type 1 ($AT_1$) receptor.

BACKGROUND OF INVENTION

Angiotensin II (Ang II)—the octapeptide (Asp-Arg-Val-Tyr-Ile-His-Pro-Phe)—is a pleiotropic vasoactive peptide that binds to two distinct receptors: the Ang II type 1 ($AT_1$)and type 2 ($AT_2$) receptors. Activation of the renin-angiotensin-aldostrone system (RAAS) results in vascular hypertrophy, vasoconstriction, salt and water retention, and hypertension. These effects are mediated predominantly by $AT_1$ receptors. Other Ang II-mediated effects, including cell death, vasodilation, and natriuresis, are mediated by $AT_2$ receptor activation. The understanding of Ang II signalling mechanisms remains incomplete. $AT_1$ receptor activation triggers a variety of intracellular systems, including tyrosine kinase-induced protein phosphorylation, production of arachidonic acid metabolites, alteration of reactive oxidant species activities, and fluxes in intracellular $Ca^{2+}$ concentrations. $AT_2$ receptor activation leads to stimulation of bradykinin, nitric oxide production, and prostaglandin metabolism, which are, in large part, opposite to the effects of the $AT_1$ receptor. (See: Berry C, Touyz R, Dominiczak A F, Webb R C, Johns D G.: Am J Physiol Heart Circ Physiol. 2001 December; 281 (6): H2337-65. Angiotensin receptors: signalling, vascular pathophysiology, and interactions with ceramide).

Ang II is the active component of the renin-angiotensin-aldosterone system (RAAS). It plays an important physiological role in the regulation of blood pressure, plasma volume, sympathetic nervous activity, and thirst responses. Ang II also has a pathophysiological role in cardiac hypertrophy, myocardial infarction, hypertension, chronic obstructive pulmonary disease, liver fibrosis and atherosclerosis. It is produced systemically via the classical RAAS and locally via tissue RAAS. In the classical RAAS, circulating renal-derived renin cleaves hepatic-derived angiotensinogen to form the decapeptide Ang I, which is converted by ACE in the lungs to the active Ang II. Ang I can also be processed into the heptapeptide Ang-(1-7) by tissue endopeptidases.

Figure 1:
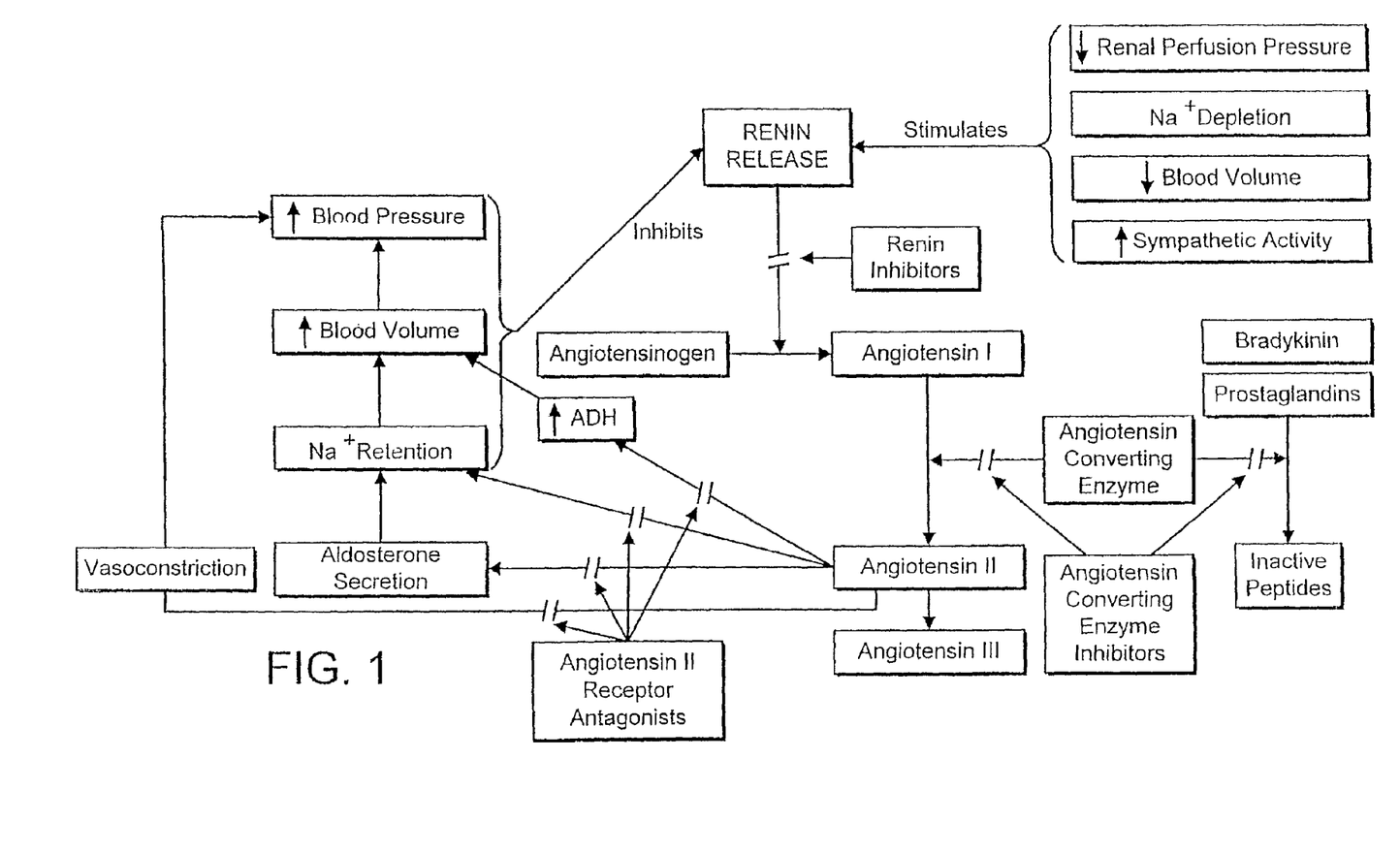
FIG. 1 illustrates the rennin-angiotensin-aldosterone system (RAAS).

The RAAS system is illustrated schematically in FIG. 1 hereto which is based on FIG. 1 in the article by Foote et al. in Ann. Pharmacother. 27: 1495-1503 (1993).

In addition to the RAAS playing an important role in the normal cardiovascular homeostasis, over activity of the RAAS has been implicated in the development of various cardiovascular diseases, such as hypertension, congestive heart failure, coronary ischemia and renal insufficiency. After myocardial infarction (MI), RAAS becomes activated. Specifically the $AT_1$ receptor seems to play a prominent role in post-MI remodelling, since $AT_1$ receptor expression is increased after MI and in left ventricular dysfunction. Therefore drugs that interfere with RAAS, such as ACE inhibitors and $AT_1$ receptor antagonists have been shown to be of great therapeutic benefit in the treatment of such cardiovascular disorders.

The anatomic coincidence between the expression of ACE and the $AT_1$ receptors with normal and pathological expressions of collagen formation is evident. High-density ACE and Ang II receptor binding are markers of active collagen turnover. Alfa-SMA-containing, fibroblast-like cells, found within valve leaflets, adventitia, and various sites of fibrous tissue formation, express genes encoding for ACE, $AT_1$ receptors, and fibrillar collagens. Myofibroblasts, MyoFbs, could therefore be considered a "metabolic entity" regulating their own collagen turnover.

ACE binding density is related primary to the presence of myoFbs. The disappearance of ACE-positive cells or a reduction in their absolute number would reduce ACE binding density at sites of fibrosis. Such is the case with old sarcoid granulomas. Both ACE and Ang II receptor binding densities in the infracted rat heart remain high for many months after the MI, as does ACE activity. Each is in the keeping with the persistence of myoFbs at the infracted site. (Weber, K. T.: Extracellular Matrix Remodelling in Heart Failure: A Role for De Novo Angiotensin II Generation. Circulation, Volume 96(11), Dec. 2, 1997, 4065-4082.)

For heart, kidneys, lungs and liver alike, fibrosis represents a common pathway to their failure. Understanding pathophysiologic mechanisms involved in organ fibrosis are therefore of considerable interest, particularly given the potential for protective pharmacological strategies. Tissue repair involves inflammatory cells, including members of the monocyte/macrophage lineage, integral to initiating the repair process; and myofibroblasts, phenotypically transformed interstitial fibroblasts, responsible for collagen turnover and fibrous tissue formation. Each of these cellular events in the microenvironment of repair are associated with molecular events that lead to the de novo generation of Ang II. In an autocrine/paracrine manner, this peptide regulates expression of Transforming growth factor beta 1, TGF-beta 1, via angiotensin ($AT_1$) receptor-ligand binding. It is this cytokine that contributes to phenotypic conversion of fibroblasts to myofibroblasts (myoFb) and regulates myofibroblast turnover of collagen. ACE inhibition or $AT_1$ receptor antagonisms each prevent many of these molecular and cellular responses that eventuate in fibrosis and therefore have been found to be protective interventions. (See: Weber K T. Fibrosis, a common pathway to organ failure: angiotensin II and tissue repair. Semin Nephrol. 1997 September; 17(5):467-91 and references therein).

Ang II may regulate tissue fibrosis via the activation of mesenchymal cells. For example, Ang II stimulates the proliferation of cardiac fibroblasts in vitro via activation of $AT_1$. The presence of $AT_1$ receptors has also been demonstrated on cardiac fibroblasts in vitro. Most of the profibrotic effects of Ang II appear to be mediated via this receptor; however, increased AT$_2$ expression on cardiac fibroblasts has been detected in hypertrophied human heart, and the balance between the expression of these two subtypes may be critical in determining the response to Ang II. (See: Am. J. Respir. Crit. Care Med., Volume 161, Number 6, June 2000, 1999-2004 Angiotensin II Is Mitogenic for Human Lung Fibroblasts via Activation of the Type 1 Receptor Richard P. Marshall, Robin J. McAnulty, and Geoffrey J. Laurent and references therein).

The Ang II receptors can be distinguished according to inhibition by specific antagonists. AT$_1$ receptors are selectively antagonized by biphenylimidazoles, such as Losartan, whereas tetrahydroimidazopyridines specifically inhibit AT$_2$ receptors. The AT$_2$ receptor may also be selectively activated by CGP-42112A. This is a hexapeptide analog of Ang II, which may also inhibit the AT$_2$ receptor, depending on concentration). Two other angiotensin receptors have been described: AT$_3$ and AT$_4$ subtypes.

In rodents, the AT$_1$ receptor has two functionally distinct subtypes, AT$_{1A}$ and AT$_{1B}$, with >95% amino acid sequence homology.

The second major angiotensin receptor isoform is the AT$_2$ receptor. It has low amino acid sequence homology (~34%) with AT$_{1A}$ or AT$_{1B}$ receptors. Although the exact signaling pathways and the functional roles of AT$_2$ receptors are unclear, these receptors may antagonize, under physiological conditions, AT$_1$-mediated actions inhibiting cell growth and by inducing apoptosis and vasodilation. The exact role of AT$_2$ receptors in cardiovascular disease remains to be defined.

Other receptors for Ang II besides AT$_1$ and AT$_2$ are known and are generally referred to as AT$_{atypical}$ (see Kang et al., Am. Heart J. 127: 1388-1401 (1994)).

The suppression of Ang II's effects has been used therapeutically, for example in the management of hypertension and heart failure. This has been achieved in a number of ways: by the use of renin inhibitors which block the conversion of angiotensinogen to Ang I (the precursor to Ang II); by the use of angiotensin converting enzyme inhibitors (ACE-I) that block the conversion of Ang I to Ang II (and also block bioconversion of bradykinin and prostaglandins); by the use of anti-Ang II-antibodies; and by the use of Ang II-receptor antagonists.

Beta blockers are most commonly used in treatment of arrhythmias. Anti-arrhythmic drugs have had limited overall success and calcium channel blockers can sometimes induce arrhythmias. No single agent shows superiority, with the possible exception of amiodarone. Short-term anti-arrhythmic benefit has been found to be offset by, depending on the specific drug, neutral or negative effects on mortality (Sanguinetti M C and Bennett, P B: Anti-arrhythmic drug target choices and screening. Circulation 2003, 93(6): 491-9257-263). Clearly better anti-arrhythmic drugs are needed.

A publication in Lancet (Lindholm, L H et al. Effect of Losartan on sudden cardiac death in people with diabetes: data from the LIFE study, The Lancet, 2003, 362: 619-620) revealed that AT$_1$ receptor antagonists in addition of being generally favourable to patients with CHF, also reduce the incidence of sudden cardiac death. There exist a few studies showing that AT$_1$ antagonists have an anti-arrhythmia effect on arrhythmias induced by myocardial infarct or in reperfusion after ligation of LAD (Harada K et al. Angiotensin II Type 1a Receptor is involved in the occurrence of reperfusion arrhythmias, Circulation, 1998, 97:315-317, Ozer M K et al. Effects of Captopril and Losartan on myocardial ischemia-reperfusion induced arrhythmias and necrosis in rats, Pharmacological research, 2002, 45 (4), 257-263, Lynch J J et al. EXP3174, The AII antagonist human metabolite of Losartan, but not Losartan nor the Angiotensin-converting enzyme inhibitor captopril, prevents the development of lethal ischemic arrhythmias in a canine model of recent myocardial infarction, JACC, 1999, 34 876-884).

Ang II may be turned into potent antagonists or partial antagonists by changes in their amino acid composition. For instance substituting phenylalanine in position 8 with isoleucine and aspartic acid in position 1 with sarcosine changes the peptide into a potent antagonist.

The specificity towards the AT$_1$ receptor may be increased by cyclisation or bridging of the amino acids in position 3 and 5. Similarly introducing sarcosine in position 1 and glycine in position 8 makes the peptide into a AT$_1$ selective antagonist (See R C Speth. Sarcosine 11, glycine 8 angiotensin II is an AT$_1$ angiotensin II receptor subtype selective anatagonist). Regulatory peptides 115 (2003) 203-209)

As mentioned above, the natural ligand to the AT$_1$ receptor is the octapeptide AngII, Asp-Arg-Val-Tyr-Ile-His-Pro-Phe, which binds to the AT$_1$ receptor in the nano-mole range.

When modifying a naturally binding ligand to a receptor by the binding of a moiety, in particularly with moieties that are relatively large and relatively bulky, the affinity of the peptide vector is frequently compromised.

DESCRIPTION OF RELATED ART

WO 98/18496 (Nycomed Imaging AS) discloses contrast agents comprising a vector-linker-reporter construct where the vector comprises angiotensin or a peptidic angiotensin derivative.

U.S. Pat. No. 4,411,881 (New England Nuclear Corporation) reads on stabilization of radio-labelled compounds. Examples of radio-labelled compounds include e.g. Angiotensin II (5-L-isoleucine) [tyrosyl-$^{125}$I]-(monoiodinated).

SUMMARY OF INVENTION

The present invention provides pharmaceuticals useful in the treatment of heart failure, cardiac arrhythmias and other diseases were fibrosis is prominent such as in COPD, liver fibrosis, and atherosclerosis comprising a peptidic moiety, Ang I or a derivative thereof, that is converted by ACE to a targeting imaging agent and a targeting pharmaceutical for treatment of disease, that demonstrate a higher binding affinity to the AT$_1$ receptor than the native octapeptide Ang II. The pharmaceutical should demonstrate antagonistic activity.

Further the present invention provides pharmaceuticals useful in the diagnosis of heart failure and other diseases were fibrosis is prominent such as in COPD, liver fibrosis, and arteriosclerosis comprising a targeting moiety incorporating an imageable moiety. The imageable moiety can be any imageable moiety which when administered to a subject can generate an image of at least a part of said subject to which said pharmaceutical has distributed, e.g. by radio imaging, SPECT, PET, MRI, X-ray, optical imaging (OI), ultrasound (US), electrical impedance or magnetometric imaging modalities. The peptide part of the pharmaceuticals of the present invention is Ang I or a derivative thereof, which is converted into Ang II or a derivative thereof by ACE in vivo. After cleavage with ACE the pharmaceutical is a targeting imaging agent and/or a targeting pharmaceutical for treatment of disease. The targeting moiety incorporating the imageable moiety demonstrate a higher binding affinity to the AT$_1$ receptor than the Ang II and preferably act as an antagonist although a weak agonistic activity may also be acceptable.

The new pharmaceuticals can hence be used sequentially or concurrently as a therapeutic agent when carrying a suitable imageable moiety for diagnostic imaging.

Further embodiments of the invention comprise providing methods of treatment of hypertension, fibrosis, COPD and related diseases and methods of imaging of heart failure and fibrosis and also methods of monitoring of progression of treatment for such diseases and disorders as well as for related vascular diseases and disorders. The invention further provides novel pharmaceutical compositions and precursors for the preparation of diagnostic agents. Kits of diagnostic agents, in particular kits for the preparation of radiopharmaceutical diagnostic agents are also provided.

The pharmaceuticals of the invention comprise a peptide V, optionally a linker L and a moiety Z and can be visualised by formula (I)

Z—L-V    (I)

wherein

V denotes a peptide with a binding sequence -$X^1$-$X^2$-Val-Tyr-Ile-His-Pro-$X^8$-$X^9$-$X^{10}$, L denotes a bond or a linker, Z denotes a group that optionally can carry an imaging moiety M, $X^1$ denotes an amino acid, $X^2$ denotes Arg, N-alkylated Arg, or a mimetic of Arg, $X^8$ denotes Gly or Phe or an amino acid containing an aromatic or aliphatic side-chain, $X^9$ and $X^{10}$ denote, independent of each other, Pro, Arg, His, Ala, Phe, Glu, Leu, Val, Ile, Met, Trp, Asp or Lys and where $X^8$, $X^9$ and $X^{10}$ together constitute an ACE cleavage site and wherein the residues Val and Ile at position 3 and 5 respectively may optionally be replaced with amino acids capable of forming a bridge, Z forms a bond with the amino acid $X^1$ optionally through the linker L, and M where present denotes an imageable moiety capable of detection either directly or indirectly in a diagnostic imaging procedure.

In areas of collagen formation, both in normal and pathological collagen formation, ACE and $AT_1$ receptor expressions are increased. The pharmaceuticals of the present invention comprise a peptidic moiety of Ang I or a derivative thereof including an ACE cleavage site. This Ang I is converted into Ang II by cleavage by ACE in vivo. We have surprisingly found that such Ang II resulting from the cleavage of Ang I with ACE and which is substituted in specific positions of the peptide not only retains its binding capability but surprisingly increases its affinity for the Ang II receptors, in particular to the $AT_1$ receptor.

The pharmaceuticals of the present invention are concerted into their active form, where the peptidic moiety is an Ang II analogue, by ACE on a site where the $AT_1$ receptor density is elevated. The co-localisation of increased ACE and $AT_1$ receptor densities in the sites of fibrous tissue formation give the present pharmaceutical the advantage that the active targeting form is formed at the site where the $AT_1$ receptor density is high. This prevents unwanted systemic effects in other parts of the body since the active Ang II analogues become $AT_1$ receptor bound on the site of formation and are not circulated.

The pharmaceuticals of the present invention show a better signal noise level i.e. heart to liver ratio, in imaging.

DETAILED DESCRIPTION OF THE INVENTION

The invention is described in the patent claims. Specific features of the invention are outlined in the following detailed description and the Examples.

In the targeting moiety of the formula (I) above V denotes the peptide sequence -$X^1$-$X^2$-Val-Tyr-Ile-His-Pro-$X^8$-$X^9$-$X^{10}$.

In the peptide V of formula (I) the amino acids are L-amino acids as in the native Ang I where not defined otherwise.

The three letter abbreviations used for the amino acids have the following meaning:

Arg—Arginine
Asp—Aspartic acid
Cys—Cysteine
Hcy—Homocysteine
Gly—Glycine
Sar—Sarcosine
Val—Valine
Tyr—Tyrosine
Ile—Isoleucine
Glu—Glutamic acid
Lys—Lysine
His—Histidine
Ala—Alanine
Leu—Leucine
Ile—Isoleucine
Met—Methionine
Trp—Tryptophan
Pro—Proline
Phe—Phenylalanine
Abu—2-Amino-butyric acid
Nva—2-Amino-pentanoic acid
Nle—2-Amino-hexanoic acid
Phg—2-Amino-2-phenyl acetic acid
Hph—2-Amino-4-phenyl butanoic acid
Bip—2-Amino-3-biphenyl propionic acid
Nal—2-Amino-3-naphtyl propionic acid
Cha—2-Amino-3-cyclohexyl propionic acid The amino acids of V preferably are independently selected such that $X^1$ denotes —$NY_1$—$(CH_2)_m$—CO— where m is an integer from 1 to 10 and $Y_1$ is H or an alkyl or aryl containing substituent, most preferred Gly $X^2$ denotes Arg or N-Methyl-Arg or the Arg mimetics Phe[4-guanidino] and Gly-4-piperidyl[N-amidino], $X^8$ denotes an amino acid with an aromatic or aliphatic side chain; preferred Phe, Phg, Hph, Bip, Ala, Gly, Tyr, His, Trp or Nal; most preferred Phe, $X^9$ and $X^{10}$ denote, independent of each other, Pro, Arg, His, Ala, Phe, Glu, Leu, Val, Ile, Met, Trp, Asp or Lys Still further preferred are pharmaceuticals where $X^1$ denotes Gly, $X^2$ denotes Arg and $X^8$ denotes Phe, $X^9$—denotes Phe, Leu or Ala and $X^{10}$—denotes Phe, Ala or His.

If the amino acids at position 3 and 5 are selected to form a bridging unit the bridge preferably containing a —$CH_2$—$CH_2$—, —S—$CH_2$—, —S—$CH_2$—S—, lactam or —S—S— unit. More preferred the covalent bond is a disulfide bond formed by oxidation of 2 cysteine or homocysteine pairings.

Examples of suitable linkers L are described in WO 98/18496 and in WO 01/77145 (pages 23 to 27) the content of which are hereby incorporated by reference. L may preferably represent a polyalkylene glycol unit such as polyethylene glycol (PEG) and polypropylene glycol (PPG), a carbohydrate, dextran, 1 to 10 amino acids or 1-5 amino acids. The linker may also serve as a biomodifier as described e.g. in WO 03/006491.

The linker L may also be derived from alkylamines or arylamines preferably compounds of the formula NH—(CH2)m- optionally combined with —CO—(CH2)m-CO— where m denotes a positive integer from 1 to 10.

The linker may also comprise one or more units of PEG as defined in formula IV hereinafter wherein n is an integer from 1 to 10.

Most preferred are linkers defined by formula (X) and (VI):

Z may also denote a polyalkylene glycol such as polyethylene glycol (PEG) and polypropylene glycol (PPG), a carbohydrate such as mono or polysaccharides all having a molecular weight in excess of 50 D. Polyalkylene glycols can additionally act as biomodifiers.

Specifically Z denotes a chelating agent such as acyclic or cyclic polyaminocarboxylates (e.g. DTPA, DTPA-BMA, DOTA and DO3A) as described e.g. in U.S. Pat. No. 4,647,447 (Schering AG) and WO 86/02841 (Nycomed Salutar, Inc.) which is hereby incorporated by reference. Further chelating agents comprises aminethiols such as diaminedithiols, amineoximes and hydrazines and related agents as described in WO 01/77145 (see Table I therein) which is hereby incorporated by reference. The chelating agent of formula VIII hereinafter, cPN216, is particularly preferred.

For pharmaceuticals useful in treatment Z can be any entity as described above.

For pharmaceuticals useful in diagnosis and particularly in in vivo diagnosis the moiety Z must be able to carry the Formula (X)

Formula (VI)

The moiety Z comprises a non-peptidic moiety having a molecular weight of more than 50 D (Dalton), more preferably between 100 and 1000 D and still more preferably between 300 to 700 D. The moiety Z can be any pharmaceutically acceptable chemical entity provided that the resulting targeting moiety, after cleavage with ACE, of formula (I) demonstrates a higher binding affinity to the $AT_1$ receptor than the native ligand Ang II. More specifically Z denotes an organic group having a suitable functional group such that Z can be reacted either with the linker L or directly with the peptide V to form a stable covalent bond.

Z can denote a straight or branched hydrocarbyl group optionally containing one or more double or triple bonds and optionally substituted by halogen, oxygen, sulphur of phosphorous atoms or optionally including heteroatoms such as oxygen, nitrogen or sulphur. More specifically the hydrocarbyl group can denote a substituted or unsubstituted alkyl, alkenyl, alkynyl groups having a molecular weight of at least 50 D.

Z can also denote one or more linked carbocyclic residues comprising monocyclic, bicyclic or tricyclic ring systems which can be saturated, partially unsaturated or aromatic and which can be substituted or unsubstituted and having a molecular weight of at least 50 D. Examples of such ring systems are aryl, aralkyl, cyclohexyl, adamantyl and naphthyl.

Z can further denote one or more linked heterocyclic compounds such as 5, 6, 7, 8, 9 or 10-membered ring systems which can be monocyclic, bicyclic or tricyclic and can contain one or more N, O, S and P as heteroatoms. Such ring systems can also be linked to hydrocarbyl and carbocyclic groups and defined above or fused to carbocyclic groups. Examples of such groups acridinyl, benzofuranyl, indolyl, pyridyl, piperidinyl, morphoridinyl and thienyl.

imageable moiety or moieties denoted M. By carrying is meant any form of association between the moiety Z and M such as a chemical bond, e.g. covalent bond or electrovalent or ionic bonds or by absorption or any other type of association.

In a preferred embodiment one moiety Z is covalently bound directly to $X^1$ forming an N-alkyl glycine unit.

Chelating agents of formula (VII) and (VIII) hereinafter are also particularly preferred.

M can be any imageable moiety. The nature of M will depend of the imaging modality utilised in the diagnosis. M must be capable of detection either directly or indirectly in an in vivo diagnostic imaging procedure. e.g. moieties which emit or may be caused to emit detectable radiation (e.g. by radioactive decay, fluorescence excitation, spin resonance excitation, etc.), moieties which affect local electromagnetic fields (e.g. paramagnetic, superparamagnetic, ferrimagnetic or ferromagnetic species), moieties which absorb or scatter radiation energy (e.g. chromophores, particles (including gas or liquid containing vesicles), heavy elements and compounds thereof, etc.), and moieties which generate a detectable substance (e.g. gas microbubble generators).

A wide range of suitable imageable moieties are known from e.g. WO 98/18496, the content of which is incorporated by reference.

Imaging modalities and imageable moieties M are described in more detail hereinafter:

In a first embodiment, the pharmaceuticals of formula (I) comprises a moiety Z carrying one or more imageable moieties M useful in the Radio and SPECT imaging modality. Preferably M is a gamma emitter with low or no alpha- and beta-emission and with a half-life of more than one hour.

Preferred groups M are the radionuclides $^{87}$Ga, $^{111}$In, $^{123}$I, $^{125}$I, $^{131}$I, $^{81m}$Kr, $^{99}$Mo, $^{99m}$Tc, $^{201}$Tl and $^{133}$Xe. Most preferred is $^{99m}$Tc.

When M denotes a metallic radionuclide then Z denotes a chelating agent suitable for forming a stable chelate with M. Such chelating agents are well known from the state of art and typical examples of such chelating agents are described in Table I of WO 01/77145.

Particularly preferred are chelating agents of formula (VII):

wherein:
each $R^1$, $R^2$, $R^3$ and $R^4$ is independently H or $C_{1-10}$ alkyl, $C_{1-10}$ alkylaryl, $C_{1-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached form a carbocyclic, heterocyclic, saturated or unsaturated ring.

More particularly preferred are chelating agents of formula (VII) where $R^1$, $R^2$ and $R^3$ are hydrogen or methyl groups and $R^4$ is an alkylamine group, most specifically a compound of formula (VIII), herein denoted cPN216.

Formula (VIII)

Most preferred for Z is when the chelating agent is cPN216 then the imaging moiety M is $^{99m}$Tc.

Non-metal radionuclides such as $^{123}$I, $^{125}$I and $^{131}$I may be covalently linked to the moiety Z by a substitution or addition reaction well known from the state of art.

In a second embodiment, the pharmaceuticals of formula (I) comprises a moiety Z carrying one or more imageable moieties M useful in the PET imaging modality. M then denotes a radioemitter with positron-emitting properties. Preferred groups M are the radionuclides $^{11}$C, $^{18}$F, $^{68}$Ga, $^{13}$N, $^{15}$O and $^{82}$Rb. $^{18}$F is specifically preferred.

When M denotes a metallic radionuclide then Z denotes a chelating agent suitable for forming a stable chelate with M. Such chelating agents are well known from the state of art and typical examples of such chelating agents are described in Table I of WO 01/77145 and to the previous part on Radio and SPECT imaging.

In another preferred embodiment Z is the DOTA chelating agent and M is $^{68}$Ga which can be readily introduced in to the chelate using microwave chemistry.

Non-metal radionuclides such as $^{18}$F may be covalently linked to the moiety Z by a substitution or addition reaction well known from the state of art and also described e.g. in WO03/080544 which is hereby incorporated by reference.

In a third embodiment, the pharmaceuticals of formula (I) comprises a moiety Z carrying one or more imageable moieties M useful in the MR imaging modality. M here denotes a paramagnetic metal such those mentioned in U.S. Pat. No. 4,647,447, $Gd^{3+}$, $Dy^{3+}$, $Fe^{3+}$ and $Mn^{2+}$ are particularly preferred and Z denotes a chelating agent, in particular a chelating agent such as acyclic or cyclic polyaminocarboxylates (e.g. DTPA, DTPA-BMA, DOTA and DO3A) as described e.g. in U.S. Pat. No. 4,647,447 and WO 86/02841. M may also denote metal oxides such as superparamagnetic, ferrimagnetic or ferromagnetic species which are absorbed by Z, e.g. such that Z function as a coating to the metal oxide. Metal oxides for use as MR imaging agents are described e.g. in U.S. Pat. No. 6,230,777 which is hereby incorporated by reference.

In a fourth embodiment the pharmaceuticals of formula (I) comprises a moiety Z carrying one or more imageable moieties M useful in the X-ray imaging modality. M here denotes a heavy metal such as W, Au and Bi preferably in the form of oxides which may be absorbed to Z. Iodinated aryl derivatives are particularly well known as X-ray contrast agents, e.g. lopamiron™ and Omnipaque™. These agents can be linked via their amide or amine functions to the peptide V.

Ultrasound imaging agents in the form of gas filled microvesicles can be utilised in the imaging of receptors e.g. when they are functionalised for binding to a peptide as described in the state of art e.g. in WO98/18500.

Use of imaging agents for optical imaging with affinity for biological targets can be provided following the procedures in the state of art e.g. as described in WO 96/17628 of Schering AG which is herewith incorporated by reference.

The pharmaceutical of formula (I) may be further modified by the attachment of one or more biomodifier groups such as polyalkylene glycol unit e.g. polyethylene glycol (PEG) and polypropylene glycol (PPG). Examples of biomodifier groups are described in WO 03/006491 the content of which is hereby incorporated by reference. The biomodifier groups can be linked to any position in the V and L groups of formula (I) as long as it does not significantly affect in a negative way the cleavage by ACE or the cleaved compound's ability to link to the target receptor.

The biomodifier is preferably based on a monodisperse PEG building block comprising 1 to 10 units of said building block, said biomodifier having the function of modifying the pharmacokinetics and blood clearance rates of the said agents. In a preferred embodiment of this invention, the compound of formula IV, represents a biomodifier unit comprised of polymerisation of the monodisperse PEG-like structure, 17-amino-5-oxo-6-aza-3,9,12,15-tetraoxaheptadecanoic acid.

wherein n equals an integer from 1 to 10 and where the C-terminal unit forms an amide bond.

Examples of pharmaceuticals of formula (I) are represented by:

Compounds of the formula (II) and (III):

where m is an integer of between 1 and 5 and Z, $X^1$, $X^2$, $X^8$, $X^9$ and $X^{10}$ are as defined previously.

Compounds defined by formula Xa and VIa:

where Z and V are as defined previously.

Compounds of the formula (IX):

suitable carried out by injection or infusion of the formulation such as an aqueous solution. The formulation may contain one or more pharmaceutical acceptable additives and/or excipients e.g. buffers; solubilisers such as cyclodextrins; or surfactants such as Pluronic, Tween or phospholipids. Further, stabilisers or antioxidants such as ascorbic acid, gentisic acid or para-aminobenzoic acid and also bulking agents for lyophilisation such as sodium chloride or mannitol may be added.

The pharmaceuticals of formula (I) are useful in treatment and diagnosis of heart failure, cardiac arrhythmias and other diseases where fibrosis is prominent specifically COPD, liver fibrosis and atherosclerosis. These pharmaceuticals are also useful in the monitoring of therapeutic treatment.

where $Y_2$ is alkyl, aryl or a short PEG containing moiety and $Y_2$ is preferably —CH2-CH2-CH2- and $X^8$, $X^9$ and $X^{10}$ is as defined above.

As noted above, for use in in vivo diagnosis the chelates of these compounds with $^{99m}$Tc or $^{18}$F are particularly preferred.

The pharmaceutical of formula (I) are preferably administered as a pharmaceutical formulation comprising the pharmaceuticals of formula (I) in a form suitable for administration to a mammal, such as a human. The administration is Further aspects of the invention are methods of treatment and in vivo diagnosis of heart failure, cardiac arrhythmias and other diseases where fibrosis is prominent specifically COPD, liver fibrosis and atherosclerosis.

Method of treatment of heart failure and other diseases where fibrosis is prominent specifically COPD, liver fibrosis and atherosclerosis in a subject comprising administration of the pharmaceuticals of formula (I) to said subject.

Method of in vivo diagnosis of heart failure and other diseases where fibrosis is prominent specifically COPD, liver fibrosis and atherosclerosis in a subject comprising administration of the pharmaceuticals of formula (I) followed by generation of an image of part or all of said subject.

Method for the monitoring progression of the treatment of heart failure and other diseases where fibrosis is prominent specifically COPD, liver fibrosis and atherosclerosis in a subject comprising administration of pharmaceuticals of formula (I) followed by the generation of an image of part or all of said subject.

In a still further aspect a kit for the preparation of a radiopharmaceutical composition of formula (I) comprising a peptide-chelate conjugate and a reducing agent is provided. Preferably the reducing agent of the kit is a stannous salt. The kit may also comprise one or more stabilisers, antioxidants, bulking agents for lyophilisation and solubilisers.

General Procedures for the Preparation of the Pharmaceuticals and its Precursors The abbreviations used have the following meanings:
Fmoc: 9-fluorenylmethoxycarbonyl
Boc: t-butyloxycarbonyl
tBu: t-butyl
Trt: trityl
Pmc: 2,2,5,7,8-pentamethylchroman-6-sulfonyl
TFA: trifluoroacetic acid
HBTU: O-Benzotriazol-1-yl-N,N,N',N'-tetramethyluronium hexafluorophosohate
DMF: dimethylformamide
NMP: N-methylpyrrolidone
TIS: triisopropylsilane
NHS: N-hydroxysuccinimidyl
NMM: N-methylmorpholine
RP-HPLC: reversed phase high pressure liquid chromatography
Wang resin: p-benzyloxybenzyl alcohol resin Synthesis of V:

The peptides V of the present invention can be synthesised using all the known methods of chemical synthesis but particularly useful is the solid-phase methodology of Merrifield employing an automated peptide synthesizer (J. Am. Chem. Soc., 85: 2149 (1964)). Typically, the desired sequences are assembled by solid-phase peptide synthesis. Standard procedures for the synthesis strategy employed for the examples of this invention are described in E. Atherton & R. C. Sheppard, "Solid phase peptide synthesis: a practical approach", 1989, IRL Press, Oxford.

For example, a resin with an acid-labile linker group, to which the desired amino-protected C-terminal amino acid residue has been esterified, is used. The amino protecting group is then removed and the second amino acid in the sequence is coupled using a suitable condensation reagent. Amino acids with semi-permanent amino protecting groups and permanent protecting groups for the functional side chains are employed. Amino-deprotection and coupling cycles are then repeated in alternating steps until the sequence of interest is assembled.

Alternatively, the peptides V can be synthesised through solution peptide synthesis methods known in the art, either in a step-wise manner from the carboxyl terminus and/or through the application of segment condensation or ligation methods, employing comprehensive or minimal protection strategies. Combined solution-solid phase segment condensation approaches can also be applied.

Generally, the reactive side-chain groups present (for example amino, hydroxyl, guanidino and carboxyl groups) will be protected during overall synthesis as indicated above. A wide choice of protecting groups for amino acids is known (see, e.g., Greene, T. W. & Wuts, P. G. M. (1991) Protective groups in organic synthesis, John Wiley & Sons, New York). Amino protecting groups which may be employed include 9-fluorenylmethoxycarbonyl (Fmoc) and t-butyloxycarbonyl (Boc). Side-chain protecting groups which may be employed include t-butyl (tBu), trityl (Trt), Boc, and 2,2,5,7,8-pentamethylchroman-6-sulfonyl (Pmc). It will be appreciated that a wide range of other such groups are known in the art.

Finally the permanent side-chain protecting groups are removed and the peptide is cleaved from the resin, usually simultaneously through treatment with a suitable acidic reagent, e.g. trifluoroacetic acid (TFA).

Conjugation of L to V:

L can be conjugated to V using all the known methods of chemical synthesis. Particularly useful is the nucleophile substitution reaction where a leaving group on the peptide N-terminus is replaced by a nucleophilic group on L. Such a leaving group may be a bromide attached in alpha position to a carbonyl group, and such a nucleophile may be nitrogen.

Conjugation of Z to V or to L:

Z can be conjugated directly to V using the same methods as for the conjugation of L to V. In the case where Z is attached to V via L any methods of chemical synthesis may be used in the conjugation of Z and L. Particularly useful is amide bond formation.

EXAMPLES

Example 1

Ang I Analogue for $^{99m}$Tc Labelling [SEQ ID NO 2]

cPn216-Gly-Arg-Val-Tyr-Ile-His-Pro-Phe-His-Leu-OH

MW = 1564.96
EM = 1563.94
MF = C77H121N21O14

A peptide analogue of Ang I was synthesised on an Applied Biosystems 433A peptide synthesizer starting with 0.1 mmol Fmoc-Leu-SASRIN resin. An excess of 1 mmol pre-activated amino acids (using HBTU; O-Benzotriazol-1-yl-N,N,N',N'-tetramethyluronium hexafluorophosohate) was applied in the coupling steps up to Arginine. The N-terminus was bromoacetylated using 0.5 mmol bromoacetic anhydride in DMF for 60 minutes. The bromoacetylated resin was then treated with a solution of 0.1 mmol cPn216 and 0.2 N-methylmorpholine dissolved in dimethylformamide for 60 minutes.

The simultaneous removal of side-chain protecting groups and cleavage of the peptide from the resins was carried out in 5 mL trifluoroacetic acid (TFA) containing 2.5% triisopropylsilane and 2.5% water for 60 minutes. TFA was removed in vacuo, diethyl ether added to the residue and the precipitated product washed with diethyl ether and air-dried.

Purification by preparative RP-HPLC (20-35% B over 40 min, where A=H$_2$O/0.1% TFA and B=CH$_3$CN/0.1% TFA, at a flow rate of 10 mL/min on a Vydac C18 250×21.20 mm column) of the product afforded 3 mg pure chelate-peptide conjugate. The product was analysed by analytical HPLC (conditions: Gradient, 20-35% B over 20 min where A=H$_2$O/0.1% TFA and B=CH$_3$CN/0.1% TFA; flow, 1 mL/min; column, Vydac C18 25×4.6 mm; detection, UV 214 nm; product retention time 14.9 min). Further product characterisation was carried out using electrospray mass spectrometry (MH$^+$ calculated, 1564.9; MH$^+$ found, 1564.9).

Example 1a

ACE Cleavage

ACE stock solution was prepared: 0.34 mg ACE (Sigma A-6778) was dissolved in 1 mL 200 mM HEPES adjusted to pH 7.8 using KOH.

0.1 mg of the Ang I peptide analogue was dissolved in 100 µL of the ACE stock solution and the solution incubated at room temperature. Samples (10 µL) were withdrawn from the solution, diluted with H$_2$O/0.1% TFA (400 µL) and analysed by LC-MS.

Cleavage Rates of Ang I Peptide Analogues

| Cleavage rates of Ang I peptides analogues | |
|---|---|
| | percent cleavage/time |
| Ang I | 40%/120 min |
| cPn216-Gly-Arg-Val-Tyr-Ile-His-Pro-Phe-His-Leu-OH | 40%/120 min |

Example 2

SEQ ID NO 3

N-cPn216-Gly-Arg-Val-Tyr-Ile-His-Pro-Ile-His-Leu-OH

Structure

MW = 1530.94
EM = 1529.96
MF = C74H123N21O14

Synthesis

The peptidyl resin H-Arg(Pmc)-Val-Tyr(tBu)-Ile-His(Trt)-Pro-Ile-His(Trt)-Leu-R was assembled on an Applied Biosystems 433A peptide synthesizer using Fmoc chemistry starting with 0.25 mmol Fmoc-Leu-SASRIN resin. An excess of 1 mmol pre-activated amino acids (using HBTU) was applied in the coupling steps. The resin was then transferred to a nitrogen bubbler apparatus.

Bromoacetic acid (2 mmol, 278 mg) and DCC (1 mmol, 206 mg) were dissolved in DCM (5 mL). The mixture was stirred for 15 min, precipitated DCCU filtered off and the filtrate evaporated in vacuo to dryness affording bromoacetic anhydride as a white solid. The anhydride was dissolved in DMF and added to the resin from above. The anhydride solution was removed after 30 min by filtration and the resin washed with DMF. The bromoacetylated resin (0.05 mmol) was then treated with a solution of cPn216 (NC-100676, free amine) (0.1 mmol, 34 mg) in DMF for 2 hours. The resin was finally washed with DMF and DCM and dried under a stream of nitrogen.

The simultaneous removal of the side-chain protecting groups and cleavage of the peptide from the resin was carried out in 10 mL TFA containing 2.5% TIS and 2.5% water for 90 minutes. TFA was removed in vacuo and diethyl ether added to the residue. The precipitate was washed with diethyl ether and air-dried affording 70 mg crude AH-111232.

Purification and Characterisation

Purification by preparative HPLC (gradient: 5-50% B over 40 min where A=$H_2O$/0.1% TFA and B=ACN/0.1% TFA, flow rate: 10 mL/min, column: Phenomenex Luna 5μ C18 (2) 250×21.20 mm, detection: UV 214 nm, product retention time: 27.2 min) of 70 mg of the crude material afforded 7.4 mg semi-pure AH-111232. A second purification step where TFA was replaced by HCOOH (gradient: 0-30% B, elsewhere same conditions as above) afforded 5.4 mg pure AH-111232.

The pure product was analysed by analytical HPLC (gradient: 0-30% B over 10 min where A=$H_2O$/0.1% HCOOH and B=ACN/0.1% HCOOH, flow rate: 0.3 mL/min, column: Phenomenex Luna 3μ C18 (2) 50×2 mm, detection: UV 214 nm, product retention time: 7.03 min). Further product characterisation was carried out using electrospray mass spectrometry ($MH^+$ calculated: 1531.0, $MH^+$ found: 1530.8).

Example 3

Ang I Analogue [SEQ ID NO 4]

H-Arg-Val-Tyr-Ile-His-Pro-Bip-His-Leu-OH

Structure

MW = 1257.52
EM = 1256.68
MF = C64H88N16O11

Synthesis

The peptidyl resin H-Arg(Pmc)-Val-Tyr(tBu)-Ile-His(Trt)-Pro-Bip-His(Trt)-Leu-R was assembled on an Applied Biosystems 433A peptide synthesizer using Fmoc chemistry starting with 0.25 mmol Fmoc-Leu-SASRIN resin. An excess of 1 mmol pre-activated amino acids (using HBTU) was applied in the coupling steps. The resin was then transferred to a nitrogen bubbler apparatus.

The simultaneous removal of the side-chain protecting groups and cleavage of the peptide from the resin was carried out in 5 mL TFA containing 2.5% TIS and 2.5% water for 60 minutes. TFA was removed in vacuo and diethyl ether added to the residue. The precipitate was washed with diethyl ether and air-dried affording crude AH-111415.

Characterisation

The crude product was analysed by analytical HPLC (gradient: 10-60% B over 20 min where A=$H_2O$/0.1% TFA and B=ACN/0.1% TFA, flow rate: 1 mL/min, column: Phenomenex Luna 3μ C18 (2) 250×2 mm, detection: UV 214 nm, product retention time: 14.43 min). Further product characterisation was carried out using mass spectrometry (($MH_2$)$^{2+}$ calculated: 629.3, $MH_2$)$^{2+}$ found: 629.4).

Example 4

SEQ ID NO 5

N-cPn216-Gly-Arg-Val-Tyr-Ile-His-Pro-Bip-His-Leu-OH

Structure

MW = 1641.05
EM = 1639.97
MF = C83H125N21O14

Synthesis

The resin from above, H-Arg(Pmc)-Val-Tyr(tBu)-Ile-His(Trt)-Pro-Bip-His(Trt)-Leu-R (0.25 mmol), was treated with a solution of bromoacetic anhydride (prepared as described above) dissolved in DMF for 30 minutes. The bromoacetylated resin (0.05 mmol) was then treated with a solution of cPn216 (NC-100676, free amine) (0.25 mmol, 86 mg) in THF for 60 minutes. The resin was finally washed with THF and dried under a stream of nitrogen.

The simultaneous removal of the side-chain protecting groups and cleavage of the peptide from the resin was carried out in 10 mL TFA containing 2.5% TIS and 2.5% water for 90 minutes. TFA was removed in vacuo and diethyl ether added to the residue. The precipitate was washed with diethyl ether and air-dried affording 90 mg crude AH-111453.

Purification and Characterisation

Purification by preparative HPLC (gradient: 5-50% B over 40 min where A=H$_2$O/0.1% TFA and B=ACN/0.1% TFA, flow rate: 10 mL/min, column: Phenomenex Luna 5µ C18 (2) 250×21.20 mm, detection: UV 214 nm, product retention time: 32 min) of 90 mg of the crude material afforded 34 mg semi-pure AH-111453. A second purification step where TFA was replaced by HCOOH (gradient: 0-30% B, elsewhere same conditions as above) afforded 18 mg pure AH-111453.

The pure product was analysed by analytical HPLC (gradient: 0-30% B over 10 min where A=H$_2$O/0.1% HCOOH and B=ACN/0.1% HCOOH, flow rate: 0.3 mL/min, column: Phenomenex Luna 3µ C18 (2) 50×2 mm, detection: UV 214 nm, product retention time: 7.40 min). Further product characterisation was carried out using electrospray mass spectrometry (MH$^+$ calculated: 1641.0, MH$^+$ found: 1640.7).

Example 5

SEQ ID NO 6

N-cPn216-Gly-Arg-Val-Tyr-Ile-His-Pro-Hph-His-Leu-OH

Structure solution was removed after 30 min by filtration and the resin washed with DMF. The bromoacetylated resin (0.05 mmol) was then treated with a solution of cPn216 (NC-100676) (0.25 mmol, 86 mg) in DMF for 2 hours. The resin was finally washed with DMF and DCM.

The simultaneous removal of the side-chain protecting groups and cleavage of the peptide from the resin was carried out in 10 mL TFA containing 2.5% TIS and 2.5% water for 90 minutes. TFA was removed in vacuo and diethyl ether added to the residue. The precipitate was washed with diethyl ether and air-dried affording 24 mg crude AH-111454.

Purification and Characterisation

Purification by preparative HPLC (gradient: 5-50% B over 40 min where A =H$_2$O/0.1% TFA and B=ACN/0.1% TFA, flow rate: 10 mL/min, column: Phenomenex Luna 5µ C18 (2) 250×21.20 mm, detection: UV 214 nm, product retention time: 15 min) of 24 mg of the crude material afforded 4.7 mg semi-pure AH-111454. A second purification step (same conditions as above) of 2.6 mg semi-pure peptide afforded 0.5 mg pure AH-111454.

The pure product was analysed by analytical HPLC (gradient: 10-60% B over 20 min where A=H$_2$O/0.1% TFA and

MW = 1578.98
EM = 1577.96
MF = C78H123N21O14

Synthesis

The peptidyl resin H-Arg(Pmc)-Val-Tyr(tBu)-Ile-His(Trt)-Pro-Hph-His(Trt)-Leu-R was assembled on an Applied Biosystems 433A peptide synthesizer using Fmoc chemistry starting with 0.1 mmol Tenta Gel Sac Leu-Fmoc resin. An excess of 1 mmol pre-activated amino acids (using HBTU) was applied in the coupling steps. The resin was then transferred to a nitrogen bubbler apparatus.

Bromoacetic acid (1 mmol, 139 mg) and DCC (0.5 mmol, 103 mg) were dissolved in DCM (5 mL). The mixture was stirred for 15 min, precipitated DCCU filtered off and the filtrate evaporated in vacuo to dryness affording bromoacetic anhydride as a white solid. The anhydride was dissolved in DMF and added to the resin from above. The anhydride

B=ACN/0.1% TFA, flow rate: 1 mL/min, column: Phenomenex Luna 3µ C18 (2) 250×2 mm, detection: UV 214 nm, product retention time: 12.57 min). Further product characterisation was carried out using mass spectrometry ((MH$_2$)$^{2+}$ calculated: 790.0, (MH$_2$)$^{2+}$ found: 790.0).

Example 6

SEQ ID NO 7

N-cPn216-Gly-Arg-Val-Tyr-Ile-His-Pro-Phg-His-Leu-OH

Structure

MW = 1550.93
EM = 1549.92
MF = C76H119N21O14

Synthesis

The peptidyl resin H-Arg(Pmc)-Val-Tyr(tBu)-Ile-His(Trt)-Pro-Phg-His(Trt)-Leu-R was assembled on an Applied Biosystems 433A peptide synthesizer using Fmoc chemistry starting with 0.1 mmol Tenta Gel Sac Leu-Fmoc resin. An excess of 1 mmol pre-activated amino acids (using HBTU) was applied in the coupling steps. The resin was then transferred to a nitrogen bubbler apparatus.

Bromoacetic acid (1 mmol, 139 mg) and DCC (0.5 mmol, 103 mg) were dissolved in DCM (5 mL). The mixture was stirred for 15 min, precipitated DCCU filtered off and the filtrate evaporated in vacuo to dryness affording bromoacetic anhydride as a white solid. The anhydride was dissolved in DMF and added to the resin from above. The anhydride solution was removed after 30 min by filtration and the resin washed with DMF. The bromoacetylated resin (0.05 mmol) was then treated with a solution of cPn216 (NC-100676) (0.25 mmol, 86 mg) in THF (4 ml) for 60 min. The resin was finally washed with DMF and DCM.

The simultaneous removal of the side-chain protecting groups and cleavage of the peptide from the resin was carried out in 10 mL TFA containing 2.5% TIS and 2.5% water for 90 minutes. TFA was removed in vacuo and diethyl ether added to the residue. The precipitate was washed with diethyl ether and air-dried affording 55 mg crude AH-111519.

Purification and Characterisation

Purification by preparative HPLC (gradient: 15-35% B over 40 min where A=$H_2O$/0.1% TFA and B=ACN/0.1% TFA, flow rate: 10 mL/min, column: Phenomenex Luna 5μ C18 (2) 250×21.20 mm, detection: UV 214 nm, product retention time: 26.7 min) of 30 mg of the crude material afforded 7.4 mg pure AH-111519.

The pure product was analysed by analytical HPLC (gradient: 15-35% B over 20 min where A=$H_2O$/0.1% TFA and B=ACN/0.1% TFA, flow rate: 1 mL/min, column: Phenomenex Luna 3μ C18 (2) 250×2 mm, detection: UV 214 nm, product retention time: 15.1 min). Further product characterisation was carried out using mass spectrometry (($MH_2$)$^{2+}$ calculated: 776.0, ($MH_2$)$^{2+}$ found: 775.9).

The invention claimed is:

1. A pharmaceutical characterized by general formula (I)

Z—L-V     (I)

wherein
V denotes a peptide with a binding sequence -$X^1$-$X^2$-Val-Tyr-Ile-His-Pro-$X^8$-$X^9$-$X^{10}$, (SEQ ID NO. 1)
L denotes bond or a linker,
Z denotes a chelating agent suitable for carrying a radionuclide M,
$X^1$ denotes-$NY_1$—$(CH_2)_m$—CO— where m is an integer from 1 to 10 and $Y_1$ is H or an alkyl- or aryl-containing substituent,
$X^2$ denotes Arg, N-alkylated Arg, or Phe[4-guanidino] or Gly-4-piperidyl[N-amidino],
$X^8$ denotes Gly, Phe, Phg, Hph, Bip, Ala, Tyr, His, Trp or Nal,
$X^9$ and $X^{10}$ denote, independent of each other, Pro, Arg, His, Ala, Phe, Glu, Leu, Val, Ile, Met, Trp, Asp or Lys and where $X^8$, $X^9$ and $X^{10}$ together constitute an ACE cleavage site;

and wherein the residues Val and Ile at position 3 and 5 respectively may be replaced with the amino acids cysteine or homocysteine capable of forming a bridging unit wherein the bridge contain a —$CH_2$—$CH_2$—, —S—$CH_2$—, —S—$CH_2$—S—, lactam or —S—S— unit,
Z forms a bond with the amino acid $X^1$ optionally through the linker L, and
M is selected from $^{67}$Ga, $^{111}$In, $^{81m}$Kr, $^{99}$Mo, $^{98m}$Tc, $^{201}$Tl, $^{68}$Ga and $^{82}$Rb.

2. A pharmaceutical according to claim 1 wherein the amino acid of $X^1$, $X^2$, $X^8$, $X^9$, $X^{10}$ are independently selected from
$X^1$ denoting Gly
$X^2$ denoting Arg or N-Methyl-Arg
$X^8$ denoting Phe
$X^9$ denoting Pro, Arg, His, Ala, Phe, Glu, Leu, Val, Ile, Met, Trp, Asp or Lys and
$X^{10}$ denoting Pro, Arg, His, Ala, Phe, Glu, Leu, Val, Ile, Met, Trp, Asp or Lys.

3. A pharmaceutical according to claim 1 further comprising one or more biomodifier groups of formula (IV)

(IV)

wherein n equals an integer from 1 to 10 and where the C-terminal unit forms an amide bond attached to any positions of the V and L groups of formula (I).

4. A pharmaceutical according to claim 1 wherein Z denotes the chelating agent of formula (VII)

(VII)

wherein:

each $R^1$, $R^2$, $R^3$ and $R^4$ is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached form a carbocyclic, heterocyclic, saturated or unsaturated ring.

5. A pharmaceutical according to claim 4 wherein M represents a gamma emitting moiety for Radio or SPECT imaging selected from $^{67}$Ga, $^{111}$In, $^{81m}$Kr, $^{99}$Mo, $^{99m}$Tc and $^{201}$Tl.

6. A pharmaceutical according to claim 4 wherein M represents a radio emitter with positron emitting properties for PET imaging comprising $^{68}$Ga, and $^{82}$Rb.

7. A pharmaceutical according to claim 2 wherein L denotes a bond or a linker selected from compounds of formula NH—$(CH_2)_m$—optionally combined with —CO—$(CH_2)_m$—CO where m denotes a positive integer from 1 to 10, one or more units of compounds of formula (IV) wherein n is an integer from 1 to 10, or compounds of formula (VI) or (X)

Formula (IV)

Formula (VI)

Formula (X)

8. Pharmaceutical formulation comprising a pharmaceutical of formula (I) of claim 1 together with one or more pharmaceutical acceptable additives and/or excipients.

\* \* \* \* \*